US009138678B2

(12) United States Patent
Huang et al.

(10) Patent No.: US 9,138,678 B2
(45) Date of Patent: *Sep. 22, 2015

(54) MEMBRANE-AUGMENTED DISTILLATION WITH COMPRESSION AND CONDENSATION TO SEPARATE SOLVENTS FROM WATER

(75) Inventors: Yu Huang, Palo Alto, CA (US);
Richard W. Baker, Palo Alto, CA (US);
Benjamin McCool, Naples, FL (US);
Rong Dong, Bonita Springs, FL (US)

(73) Assignees: Membrane Technology and Research, Inc., Newark, CA (US); Algenol Biofuels, Inc., Fort Myers, FL (US)

( * ) Notice: Subject to any disclaimer, the term of this patent is extended or adjusted under 35 U.S.C. 154(b) by 657 days.

This patent is subject to a terminal disclaimer.

(21) Appl. No.: 13/370,062

(22) Filed: Feb. 9, 2012

(65) Prior Publication Data
US 2012/0137727 A1    Jun. 7, 2012

Related U.S. Application Data

(63) Continuation-in-part of application No. 12/229,790, filed on Aug. 27, 2008, now Pat. No. 8,128,787, which is a continuation-in-part of application No. 12/229,802, filed on Aug. 27, 2008, now Pat. No. 8,114,255.

(51) Int. Cl.
| | | |
|---|---|---|
| *B01D 3/14* | (2006.01) | |
| *B01D 53/22* | (2006.01) | |
| *B01D 61/36* | (2006.01) | |
| *B01D 1/28* | (2006.01) | |
| *C07C 29/76* | (2006.01) | |
| *C07C 31/08* | (2006.01) | |
| *B01D 71/32* | (2006.01) | |
| *B01D 71/44* | (2006.01) | |

(52) U.S. Cl.
CPC .............. *B01D 53/228* (2013.01); *B01D 3/145* (2013.01); *B01D 61/362* (2013.01); *B01D 71/32* (2013.01); *B01D 71/44* (2013.01); *C07C 29/76* (2013.01); *C07C 31/08* (2013.01); *B01D 2311/2669* (2013.01)

(58) Field of Classification Search
CPC ........... C07C 31/08; C07C 27/28; C02F 1/04; C02F 1/041; C02F 1/448; B01D 1/2806; B01D 1/2856; B01D 1/2881; B01D 3/001–3/005; B01D 3/007; B01D 3/143–3/145; B01D 2311/02; B01D 2311/06; B01D 2311/26; B01D 2311/2669; B01D 2313/34; B01D 53/228; B01D 61/362; B01D 61/364; B01D 71/32; B01D 71/44; B01D 53/225; F24J 3/00; Y10S 203/13; Y10S 210/06; Y10S 203/08; Y10S 203/16; C12P 7/06

See application file for complete search history.

(56) References Cited

U.S. PATENT DOCUMENTS

| | | | | |
|---|---|---|---|---|
| 3,540,986 | A * | 11/1970 | Guarino | 202/187 |
| 4,217,178 | A * | 8/1980 | Katzen et al. | 203/19 |
| 4,230,535 | A * | 10/1980 | Howard | 203/26 |
| 4,294,664 | A * | 10/1981 | Anthony | 203/19 |
| 4,340,446 | A * | 7/1982 | Crawford | 203/19 |

(Continued)

*Primary Examiner* — Virginia Manoharan
(74) *Attorney, Agent, or Firm* — Timothy A. Hott; Kathi Bean; Janet Farrant

(57) ABSTRACT

Disclosed herein are processes for removing water from organic solvents, such as ethanol. The processes include distillation in two columns operated at sequentially higher pressure, followed by treatment of the overhead vapor by one or two membrane separation steps.

44 Claims, 6 Drawing Sheets

(56) References Cited

U.S. PATENT DOCUMENTS

| | | | |
|---|---|---|---|
| 4,372,822 A * | 2/1983 | Muller et al. | 203/19 |
| 4,405,409 A | 9/1983 | Tusel et al. | |
| 4,422,903 A * | 12/1983 | Messick et al. | 203/19 |
| 4,539,076 A | 9/1985 | Swain | |
| 4,978,430 A | 12/1990 | Nakagawa et al. | |
| 5,035,776 A | 7/1991 | Knapp | |
| 5,105,029 A | 4/1992 | Ninomiya et al. | |
| 5,124,004 A * | 6/1992 | Grethlein et al. | 203/19 |
| 5,232,085 A * | 8/1993 | Hayashi et al. | 202/182 |
| 6,551,466 B1 * | 4/2003 | Kresnyak et al. | 203/1 |
| 7,297,236 B1 | 11/2007 | Vander Griend | |
| 7,732,173 B2 | 6/2010 | Mairal et al. | |
| 7,744,727 B2 * | 6/2010 | Blum et al. | 203/19 |
| 8,002,874 B2 | 8/2011 | Huang et al. | |
| 2006/0070867 A1 | 4/2006 | Ikeda | |
| 2007/0000769 A1 * | 1/2007 | Brown | 203/19 |
| 2009/0008234 A1 * | 1/2009 | Tolbert et al. | 200/600 |
| 2009/0057128 A1 | 3/2009 | Vane et al. | |
| 2009/0057224 A1 | 3/2009 | Huang et al. | |
| 2011/0152584 A1 * | 6/2011 | Pasanen et al. | 568/916 |
| 2012/0010445 A1 * | 1/2012 | Johnston et al. | 568/885 |
| 2012/0048803 A1 * | 3/2012 | Shapiro | 210/640 |
| 2012/0232315 A1 * | 9/2012 | Moll et al. | 568/913 |
| 2012/0273338 A1 * | 11/2012 | Lee et al. | 203/19 |

* cited by examiner

MEMBRANE-AUGMENTED DISTILLATION WITH COMPRESSION AND CONDENSATION TO SEPARATE SOLVENTS FROM WATER

RELATED APPLICATIONS

This application claims the benefit of U.S. Pat. Nos. 8,114,255 and 8,128,787 both of which were filed Aug. 27, 2009, the disclosures of which are hereby incorporated by reference in their entireties. The invention disclosed herein was made pursuant to a master contract research agreement between Membrane Technology and Research, Inc., and Algenol Biofuels, Inc.

FIELD OF THE INVENTION

The invention relates to production and dehydration of solvents, especially alcohols. In particular, the invention relates to combinations of distillation, overhead vapor compression, and membrane separation to produce a dehydrated solvent product.

BACKGROUND OF THE INVENTION

The production of dry solvents from raw aqueous mixtures is often costly and complicated. The preparation of dry ethanol is a good example. In the conventional process, the raw fermentation broth is stripped under moderate vacuum in a beer still. Overhead vapor from the beer still is sent to a rectification column that produces an overhead product close to the azeotrope (about 93 wt % ethanol) and a bottoms product, which is essentially water. The condensed product from the top of the rectification column is evaporated under pressure and fed to a molecular sieve dryer, which produces ethanol of 99 wt %+ purity. Such a process consumes almost 100 million Btu/h to produce 50 million gallons per year of purified ethanol from a feed containing about 11 wt % ethanol. If the concentration of ethanol in the feed is lower, for example from 0.5 to 5%, the energy consumption of the processes can rise substantially, often exceeding the energy content of the dry ethanol produced.

It is known to use two distillation columns in series to separate mixtures such as organic/water mixtures. Such processes are taught in U.S. Pat. Nos. 4,539,076; 5,035,776; and 7,297,236, for example.

It is also known to use membrane separation to treat the overhead stream from a column. Such processes are taught in U.S. Pat. Nos. 4,978,430 and 7,594,981 and in U.S. Published Application No. 2009/0057128.

In addition, co-owned U.S. Pat. No. 7,732,173 teaches a process for recovering ethanol involving membrane separation, followed by dephlegmation, followed by a second membrane separation step to dehydrate the overhead stream from the dephlegmator.

U.S. Pat. No. 5,105,029 teaches the use of two columns followed by membrane separation, and U.S. Pat. No. 4,405,409 discloses the use of two membrane separation steps in series to treat a column overhead.

Specific membranes for use in dehydration of organic compounds are taught in co-owned U.S. Pat. Nos. 8,002,874 and 8,496,831.

Despite the extensive efforts represented by the prior literature, there remains a need for a process that is both energy efficient and cost effective for producing high purity dehydrated solvents, especially ethanol.

SUMMARY OF THE INVENTION

The invention is a process for dehydrating solvents, particularly solvents that are readily miscible with water. The invention can be used to concentrate alcohols in water, e.g., bioethanol, but could be used to separate many other mixtures. The process of the invention lowers the energy used to dehydrate ethanol, but could also lower the energy used in other separation processes.

The process incorporates two distillation steps in series, operated at different pressures, followed by one or two membrane separation steps. The steps are integrated in such a way as to provide an operation that has both good energy efficiency and controlled capital costs.

A basic process of the invention for recovering an organic solvent from a solvent and water mixture includes the following steps:

(a) subjecting at least a first portion of the mixture to a first distillation step, carried out by passing a first feed stream of the mixture, at a first pressure, into a first distillation column having a first reboiler system which includes a heat exchanger, to produce a solvent-enriched, first overhead vapor stream and a first bottoms stream, wherein the first bottoms stream is enriched in water compared with the first feed stream;

(b) compressing at least a portion of the first overhead vapor stream to form a compressed overhead vapor stream;

(c) recovering heat by passing at least a portion of the compressed overhead vapor stream through the first reboiler system as a heating stream;

(d) condensing at least a portion of the compressed overhead vapor stream to form a condensed overhead stream;

(e) pumping at least a portion of the condensed overhead stream to a second distillation step, carried out under a second pressure that is higher than the first pressure in a second distillation column having a second reboiler system, to produce a solvent-enriched, second overhead vapor stream and a second bottoms stream, wherein the second bottoms stream is enriched in water compared with the condensed overhead stream; and (f) performing a membrane separation step, comprising:
  (i) providing a membrane having a feed side and a permeate side, the membrane being selective in favor of water over solvent;
  (ii) passing at least a portion of the second overhead vapor stream at a feed pressure across the feed side;
  (iii) maintaining a permeate pressure on the permeate side that is lower than the feed pressure;
  (iv) withdrawing from the feed side, as a residue stream, a dehydrated product stream; and
  (v) withdrawing from the permeate side a permeate stream enriched in water compared with the second overhead vapor stream.

The first distillation step may be carried out solely as a stripping step. Alternatively, the first distillation operation may have a few trays of rectification. This column is operated at a low pressure between about 0.3 bar and about 1.2 bar.

The overhead vapor from the first column is compressed to form a compressed overhead vapor stream. Typically, the overhead vapor is compressed about 1.5-fold, which raises the dew point sufficiently that the vapor can be condensed in the stripper reboiler.

Heat can then be recovered by passing at least a portion of the compressed overhead vapor stream through a heat exchanger as a heating stream for the reboiler. The vapor condenses in the reboiler, thereby recovering all of the latent heat content of the condensing vapor. Depending on specific operating conditions, much or all of the heat necessary for the column reboiler may be obtained in this way.

The compressed overhead vapor stream is condensed to form a condensed overhead stream, which is then pumped to a pressure between about 2 bar and about 5 bar by a liquid pump and sent to a second, high-pressure stripper. The ethanol is concentrated a second time in the second stripper.

The overhead vapor from the second stripper column (containing about 40-70 wt % ethanol) is sent to the membrane unit, which produces a concentrated ethanol residue stream and a dilute, low-pressure aqueous permeate stream.

Optionally, further energy may be recovered from the process by condensing the ethanol residue vapor stream in the first low-pressure reboiler, by recirculating the aqueous membrane permeate stream back to the low-pressure column, or both. Recirculation of the permeate stream to the column is preferably done without condensation.

An embodiment of the invention in which the membrane permeate stream is recirculated to the first distillation column and/or the residue stream is recirculated to the heat exchanger comprises the following steps:

(a) subjecting at least a first portion of a solvent and water mixture to a first distillation step, carried out by passing a first feed stream of the mixture, at a first pressure, into a first distillation column having a first reboiler system which includes a first heat exchanger, to produce a solvent-enriched, first overhead vapor stream and a first bottoms stream, wherein the first bottoms stream is enriched in water compared with the first feed stream;

(b) compressing at least a portion of the first overhead vapor stream to form a compressed overhead vapor stream;

(c) recovering heat by passing at least a portion of the compressed overhead vapor stream through the first reboiler system as a heating stream;

(d) condensing at least a portion of the compressed overhead vapor stream to form a condensed overhead stream;

(e) pumping at least a portion of the condensed overhead stream to a second distillation step, carried out under a second pressure that is higher than the first pressure in a second distillation column having a second reboiler system and a reflux condenser system, to produce a solvent-enriched, second overhead vapor stream and a second bottoms stream, wherein the second bottoms stream is enriched in water compared with the condensed overhead stream;

(f) performing a membrane separation step, comprising:
(i) providing a membrane having a feed side and a permeate side, the membrane being selective in favor of water over solvent;
(ii) passing at least a portion of the second overhead vapor stream at a feed pressure across the feed side;
(iii) maintaining a permeate pressure on the permeate side that is lower than the feed pressure;
(iv) withdrawing from the feed side, as a residue stream, a dehydrated product stream; and
(v) withdrawing from the permeate side a permeate stream enriched in water compared with the second overhead vapor stream;

(g) recirculating at least a portion of one or more of the permeate stream to the first distillation step, or the residue stream to the first reboiler system as a heating stream; and (h) condensing and withdrawing at least a portion of the residue stream as a high-purity solvent stream.

Yet another embodiment of the invention uses two sequential membrane separation steps following the distillation steps. Use of two membrane separation steps, with the residue from the first step forming the feed to the second, provides greater flexibility to tailor the process to control total energy usage and compressor capacity. This embodiment comprises the following steps:

(a) subjecting at least a first portion of the mixture to a first distillation step, carried out by passing a first feed stream of the mixture, at a first pressure, into a first distillation column having a first reboiler system which includes a first heat exchanger, to produce a solvent-enriched, first overhead vapor stream and a first bottoms stream, wherein the first bottoms stream is enriched in water compared with the first feed stream;

(b) recirculating at least a portion of the first bottoms stream to the first distillation step;

(c) compressing at least a portion of the first overhead vapor stream to form a compressed overhead vapor stream;

(d) recovering heat by passing at least a portion of the compressed overhead vapor stream through the first reboiler system as a heating stream;

(e) condensing at least a portion of the compressed overhead vapor stream to form a condensed overhead stream;

(f) pumping at least a portion of the condensed overhead stream to a second distillation step, carried out under a second pressure that is higher than the first pressure in a second distillation column having a second reboiler system and a reflux condenser system, to produce a solvent-enriched, second overhead vapor stream and a second bottoms stream, wherein the second bottoms stream is enriched in water compared with the condensed overhead stream;

(g) performing a first membrane separation step, comprising:
(i) providing a first membrane having a first feed side and a first permeate side, the membrane being selective in favor of water over solvent;
(ii) passing at least a portion of the second overhead vapor stream at a first feed pressure across the first feed side;
(iii) maintaining a first permeate pressure on the first permeate side that is lower than the first feed pressure;
(iv) withdrawing from the first feed side, as a first residue stream, a dehydrated product stream; and
(v) withdrawing from the first permeate side a first permeate stream enriched in water compared with the second overhead vapor stream; and (h) performing a second membrane separation step, comprising:
(i) providing a second membrane having a second feed side and a second permeate side, the membrane being selective in favor of water over solvent;
(ii) passing at least a portion of the first residue stream at a second feed pressure across the second feed side;
(iii) maintaining a second permeate pressure on the second permeate side that is lower than the second feed pressure;
(iv) withdrawing from the second feed side, as a second residue stream, a dehydrated product stream; and
(v) withdrawing from the second permeate side a second permeate stream enriched in water compared with the first residue stream;

Optionally, the process can further include the step of recirculating at least a portion of the second permeate stream to the second distillation step.

Optionally, the processes can include steps to enhance recovery of energy in the first distillation column by recirculating at least a portion of the first permeate stream to the first distillation column, and/or recirculating at least a portion of the first residue stream as a heating stream to the first distillation step.

The processes of the invention can treat streams of any solvent/water composition, but are particularly suited for treating those in which the solvent is present at low concentrations, such as below 15 wt %, below 10 wt %, or even below 5 wt %, such as only 1 wt % or 3 wt %. For the lowest solvent concentration feeds, designs with heat recovery to the first distillation operation by recycling of the first membrane permeate or the residue stream, or designs with two membrane steps, are especially beneficial.

It is to be understood that the above summary and the following detailed description are intended to explain and illustrate the invention without restricting its scope.

DETAILED DESCRIPTION OF THE INVENTION

Figure 1:
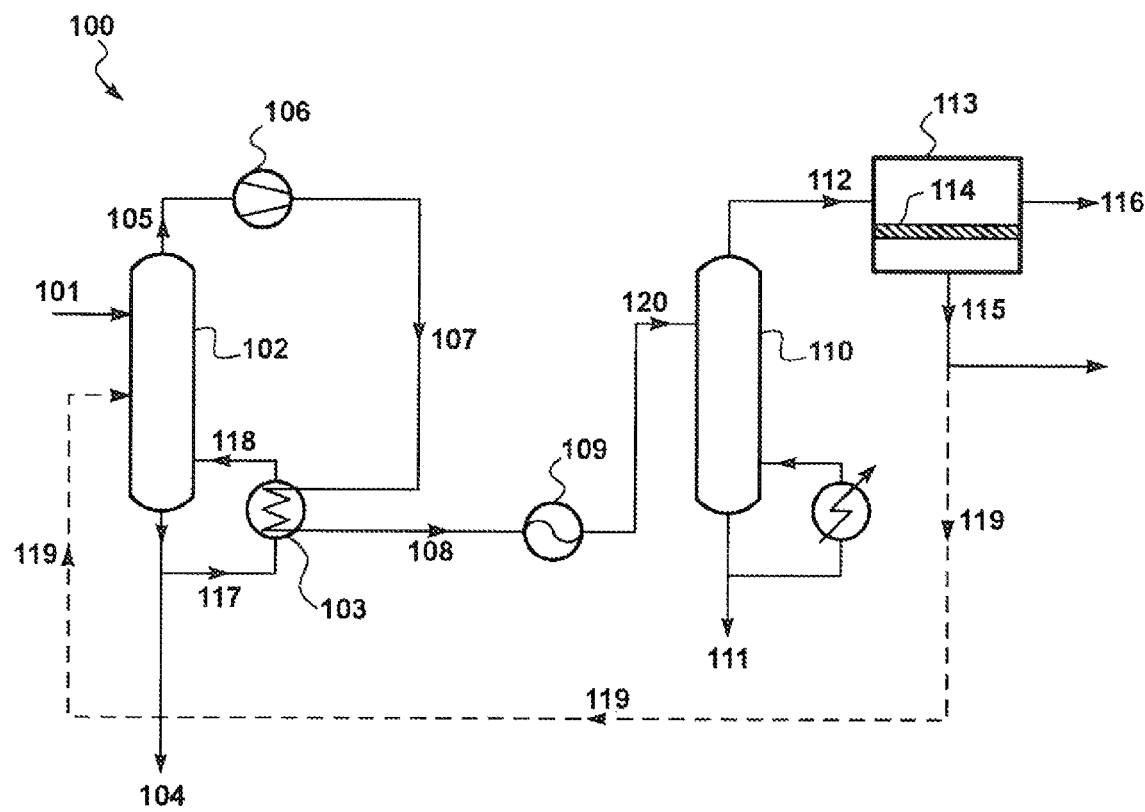
FIG. 1 is a schematic drawing showing the process flow scheme and apparatus elements for a basic embodiment of the invention, which utilizes two distillation steps followed by a membrane separation step.

The terms solvent/water solution and solvent/water mixture used herein refer to any mixtures or solutions of any organic compound and water that are generally liquid at room temperature and pressure, but that may be in the liquid or vapor phase during operation of the process.

The term selectivity as used herein refers to the selectivity of a membrane expressed as the ratio (water permeance)/(solvent permeance), as measured with membrane samples and with the solvent/water mixture of interest at the operating temperature at which the process is to be carried out.

The term rectification as used herein means performance of a distillation operation in which the distillation column uses a reboiler at the bottom of the column and a condenser or other means to create a liquid reflux stream at the top of the column. By the counter-flow of vapor up the column and liquid down the column, a separation is achieved.

The term stripping as used herein means performance of a distillation operation in which the distillation column uses a reboiler at the bottom of the column, but no condenser or other means of creating a liquid reflux stream is used at the top of the column.

The term dephlegmation as used herein means performance of a distillation operation in which the feed is introduced as a vapor at the bottom of the distillation column and the distillation column uses a condenser or other means to create a liquid reflux stream at the top of the column, but no reboiler at the bottom of the column.

The term distillation column is used generically herein to mean any column having stripping capability, rectification capability, or both, and includes dephlegmators.

All liquid mixture percentages herein are by weight unless otherwise stated. Gas or vapor mixture percentages are by weight unless otherwise stated.

The invention is a process for dehydrating solvents, particularly solvents that are readily miscible with water, and especially ethanol.

The process of the invention can be used to separate essentially any solvent/water solution or mixture. We believe the process of the invention is of particular value in separating solutions in which the organic component is in the range $C_1$-$C_6$, that is, has 1 to 6 carbon atoms, or where the solubility of water in the organic liquid at room temperature and pressure is at least about 5 wt %.

By way of example, the process of the invention is particularly useful for separating water from alcohols, ketones, aldehydes, organic acids and esters, including without limitation:

ethanol, particularly bioethanol produced from natural sources ($C_2$);

butanol ($C_4$);

acetone ($C_3$); and

ABE.

One or multiple organic compounds may be present in the mixture to be separated. A common example of an organic mixture to be treated is ABE, an acetone-butanol-ethanol mixture produced, for example, by fermentation using clostridium organisms, and used as a source of biobutanol and other valuable chemicals.

The feed stream may contain additional components besides organic solvents and water, such as inorganic salts, fermentation debris, and the like. The feed stream may come from any source, and may be subjected to pre-treatment, such as filtration, to remove contaminants before it enters the distillation column. Such contaminants may also be removed by side draws to the first and/or second column. Such side processes do not normally affect the processes of the invention.

Representative sources of the feed stream include processes that manufacture organic solvents and processes that use organic solvents. Feed streams that are particularly suited to treatment are those from the manufacture of light alcohols, ketones, aldehydes, organic acids and esters by chemical synthesis or fermentation.

Such manufacturing processes include, but are not limited to, chemical syntheses from petrochemical feedstocks, such as ethylene and propylene; fermentation of sugar-containing feedstocks; saccharification/fermentation of cellulosic and lignocellulosic feedstocks; and conversion of carbonaceous materials to syngas, followed by chemical or biochemical production of the desired solvent.

An example of such an organic solvent manufacturing process is the "Direct to Ethanol®" process practiced by Algenol (Bonita Springs, Fla.), which uses hybrid algae to produce ethanol from carbon dioxide, water, and sunlight. This process uses a proprietary flexible film photobioreactor made of plastic with special additives and coatings. The photobioreactor holds seawater that contains added nutrients, and that has been treated to remove particulates and contaminants. After inoculation with hybrid algae, carbon dioxide is introduced into the outdoor photobioreactor. After exposure to the sun, the hybrid algae perform photosynthesis and produce internal sugars that are converted into ethanol inside each algal cell. The ethanol made inside the cell diffuses through the cell wall into the cell culture medium and then evaporates, along with the water, into a headspace above the seawater. The ethanol-water vapor condenses on the inner surface of the bioreactor and is collected by gravity, concentrated, and then distilled into fuel-grade ethanol.

The solvent and water may be present in any ratio. The process is particularly useful and beneficial in treating streams in which the initial solvent concentration is less than 20 wt %, such as less than 10 wt %, 5 wt %, 3 wt %, 2 wt %, or even less. Such streams are very hard to treat in an energy efficient and cost-effective manner by prior art processes. The processes are particularly useful in treating low concentration streams where the concentration of the solvent is less than 5 wt %. With such streams, the value of the energy consumed is converted such that it can be a significant fraction of the value of the total dry solvent.

The process of the invention incorporates two distillation steps in series, operated at different pressures, followed by one or two membrane separation steps. The term "distillation column" is used herein as a generic term to describe the column, but includes stripping columns, that is, columns with reboil but no reflux, as well as full distillation columns with both reboil and reflux capabilities. The lowest energy embodiment uses two stripper columns, but some reflux could be used, especially in the second distillation column.

A schematic diagram, 100, for a basic embodiment of the invention is shown in FIG. 1. It will be appreciated by those of skill in the art that this figure, and the other figures are very simple schematic diagrams, intended to make clear the key aspects of the invention, and that an actual process train will usually include many additional components of a standard type, such as heaters, chillers, condensers, pumps, blowers, other types of separation and/or fractionation equipment, valves, switches, controllers, pressure-, temperature, level- and flow-measuring devices and the like.

In particular, the only sources of heat energy for the first column reboiler are shown as internal process streams. Additional heat energy from conventional sources, such as steam, will often be necessary to heat the reboil stream sufficiently. Also, additional heat integration may be practiced, but these techniques are familiar to those of skill in the art and have been omitted for brevity.

Referring to FIG. 1, feed stream, 101, which is usually a liquid, is passed into first distillation column, 102. In the basic embodiment shown in FIG. 1, the first column 102 takes the form of a stripping column, without a reflux condenser, although the column may optionally be equipped with a reflux system to provide rectification as well as stripping capability.

Energy for stripping column 102 is provided at least in part by reboiler heat exchanger, 103, in which a portion, 117, of the liquid bottoms stream, 104, is evaporated for return to the column as heated vapor stream, 118.

The column may be operated at any temperature and pressure appropriate to the separation that is to be carried out. Typically, the column is operated at a pressure between about 0.3 bar to about 1.2 bar. For the separation of common organic solvents as listed above, such as ethanol, it is often preferable to operate the column under a partial vacuum and at elevated temperature. For example, the column may be operated at 0.5 bar pressure with the overhead vapor being withdrawn at 70° C. or 80° C.

First overhead vapor stream, 105, is passed from the column to vapor compressor or compression step, 106. The compressor increases the pressure of the first overhead vapor stream about 1.5-fold, i.e., from 0.3-1.2 bar to about 0.45-1.8 bar.

Depending on the solvent used, overhead stream 105 will contain about 5-10 times the solvent concentration of feed stream 101. The temperature difference between the bottom and the top of first distillation column 102 is only about 3-5° C., so compressing stream 105 to only 1.5 times its original pressure is sufficient to allow the vapor to be condensed in reboiler 103. This recovers all of the latent heat of the distillation process and, as a result, the compressor 106 can be relatively small. Compressors of this type have been widely used in vapor compression systems to desalinate water and typically have an efficiency of about 75 to 80% of the theoretical ideal value.

The compressed overhead vapor stream, 107, is enriched in solvent compared with raw feed 101. The concentration of solvent in the column overhead depends on the composition of the raw feed and the operating features of the column. In general, it is preferred to operate the first column as a stripping column to deliver an overhead stream. If the feed stream contains about 1 wt % ethanol, for example, the overhead vapor stream will contain about 10 wt % ethanol. If the feed stream is more concentrated, containing 5 wt % ethanol, the overhead vapor stream will contain about 25 wt % ethanol. If the feed stream contains 10 wt % ethanol, the overhead vapor stream will contain about 45-55 wt % ethanol.

The compressed overhead vapor 107 is condensed in the first reboiler 103, liberating its latent heat to the reboiler to produce a condensed overhead stream, 108, which is then pumped through a low-energy liquid feed pump, 109, as feed, 120, to the second distillation column, 110. Feed stream 120 is about 1/10 the volume of original feed stream 101.

Liquid feed pump 109 increases the pressure of the condensed overhead stream, preferably to about 2-5 bar. If the pressure of the feed stream 120 entering second distillation column 110 is above about 5 bar, the vapor exiting the column will generally be too hot for the subsequent membrane separation step.

The pressure of the vapor in second distillation column 110 should be about 5 to 10-fold higher than the pressure of the vapor in first distillation column 102. If the pressure in second distillation column 110 is less than about 3-fold higher than the pressure in first distillation column 102, the vapor-to-pressure ratio across the membrane may not be enough to effect a good separation.

Stream 120 preferably enters second distillation column 110 at a position that matches its composition. The column produces a bottoms stream, 111, which may be sent to any destination.

Further heat integration is possible, but is not shown in the figures for clarity. For example, the distillation bottoms stream 104 is hot and can be heat-integrated with stream 101; stream 108 can also be heat-integrated with stream 101, while stream 111 may be usefully integrated with stream 120. These types of heat integration are useful in reducing the overall energy consumption of the processes, and are well-known to operators of this type of distillation equipment.

Preferably, the pressure and temperature operating conditions of the second column are set to deliver an overhead vapor stream with a solvent concentration of about 50-90 wt % solvent, and most preferably at least about 70 wt % solvent.

If the raw feed to the process is very dilute, such as containing no more than about 3 wt % solvent, it is often convenient, and can result in lower overall energy usage, to operate the second column to achieve a lower overhead concentration, in the range of 40-70 wt %, such as about 50 wt %, and to use two membrane separation steps, as discussed below with reference to the invention embodiment shown schematically in FIG. 3.

Overhead vapor from column 110 is passed as a feed stream, 112, to membrane separation step or unit, 113, containing membranes, 114, which may be of any type that provides selectivity in favor of water over the organic solvent, as discussed in further detail below.

A driving force for membrane permeation is provided by maintaining the permeate side of the membrane at a lower pressure than the feed side. Lowering the permeate pressure both increases the driving force for transmembrane permeation, increasing transmembrane flux, and increases the pressure ratio, improving the solvent/water separation performance.

The pressure difference and pressure ratio may be increased by using a vacuum pump in the permeate line to pull a vacuum on the permeate side. We have found, however, that simply cooling the permeate stream to condense the stream and create a spontaneous partial vacuum on the permeate side will provide an adequate pressure ratio in most cases, and this is our preferred mode of operation.

Condensation is achieved by cooling, typically by air or water cooling to lower the temperature to below 50° C. By operating in this manner, a pressure of 0.5 bar, 0.1 bar, or lower can be reached on the permeate side. As a typical example, the feed side may be at 3 bar total pressure and the permeate side at 0.5 bar or 0.25 bar pressure, providing a pressure ratio of 6 or 12.

As mentioned above, the membranes may be of any type that provides selectivity in favor of water over the organic solvent. In any membrane separation, the enrichment in the permeate stream of the faster permeating component (by which we mean the concentration of that component in the permeate stream divided by the concentration in the feed) can never be greater than the pressure ratio (by which we mean the total pressure on the feed side divided by the total pressure on the permeate side), irrespective of the membrane selectivity.

The membrane separation step typically operates at a modest pressure ratio, such as less than 30, so a very high selectivity is not needed for this step. In general, the preferred membrane selectivity should be less than 100, and most preferably in the range of 20-100, such as up to about 30, 50, or 60.

A selectivity higher than 100 can even be disadvantageous, as this implies a very low permeance for the slower permeating component, that is, the solvent. The membrane area requirements for the separation are controlled by the slower permeating component, so a very slow permeation rate for the solvent can lead to a very high membrane area requirement, which can greatly increase the cost of the separation process. This effect may not be very noticeable when the feed vapor contains a high concentration of water, above 20 mol %, for example. However, if the feed vapor only contains 1 to 5 mol % of water, excessively high membrane selectivities of above 60 or 70 should preferably be avoided.

Subject to the above-preference for membranes of moderate selectivity, suitable membranes that can be used may be found within several classes, including polymeric membranes and inorganic membranes.

Representative water-selective membrane types include, but are not limited to, polymeric membranes having a hydrophilic selective layer, such as polyvinyl alcohol (PVA) or cellulose acetate, or having a hydrophobic selective layer of the type taught in U.S. Pat. No. 8,496,831, co-owned with the present invention.

Yet other suitable membranes include chitosan membranes, and ion-exchange membranes, such as Nafion® membranes.

Inorganic membranes comprising hydrophilic materials may also be used as dehydration membranes. Such membranes include amorphous silica membranes and membranes including a water-permeable zeolite layer, such as ZSM-5. Various types of inorganic membranes may be purchased from Mitsui and Company (USA) of New York, Isotronics of Paradise Valley, Ariz.; Sulzer Chemtech Membrane Systems, based in Heinitz, Germany; and Pervatech BV of Enter, Netherlands.

The membrane separation unit 113 can include a single membrane module or a bank or array of membrane modules.

Water permeates the membranes 114 preferentially, to form water-enriched, solvent-depleted permeate stream, 115, which is withdrawn in vapor form. At least a portion, 119, of vapor stream 115 may optionally recirculated to the first distillation column 102. Stream 119 is preferably recirculated as a vapor to the lower part of column 102 without condensation, to recover its latent heat energy. Recycle of the permeate stream within the process also increases solvent recovery.

Returning stream 119 to column 102 as a vapor recovers the latent heat content and usually results in a lower energy process overall. Cooling and condensing the stream, however, reduces the permeate pressure. Although the latent heat is lost, the increased pressure ratio across the membrane improves performance and reduces membrane area.

The residue stream from the membrane separation step 113 is enriched in solvent compared with the feed stream, and is withdrawn as a high-purity, dehydrated solvent product stream, 116. Preferably, this stream contains at least 90 wt % solvent, and more preferably, at least 95 wt % solvent. Most preferably, the product is dehydrated to at least 98 wt % or 99 wt % solvent, or better.

The flow rate and composition of residue stream 116 depend on the operating features of the membrane separation step, such as pressure difference, pressure ratio, membrane selectivity and permeance, and membrane area. To achieve the preferred results, the membrane should typically provide a water permeance of at least about 1,000 gpu, and most preferably at least about 2,000 gpu, and a selectivity of at least 20, and preferably between 20 and 100, and the step should be operated at a pressure ratio of at least about 5 or 6.

Figure 2:
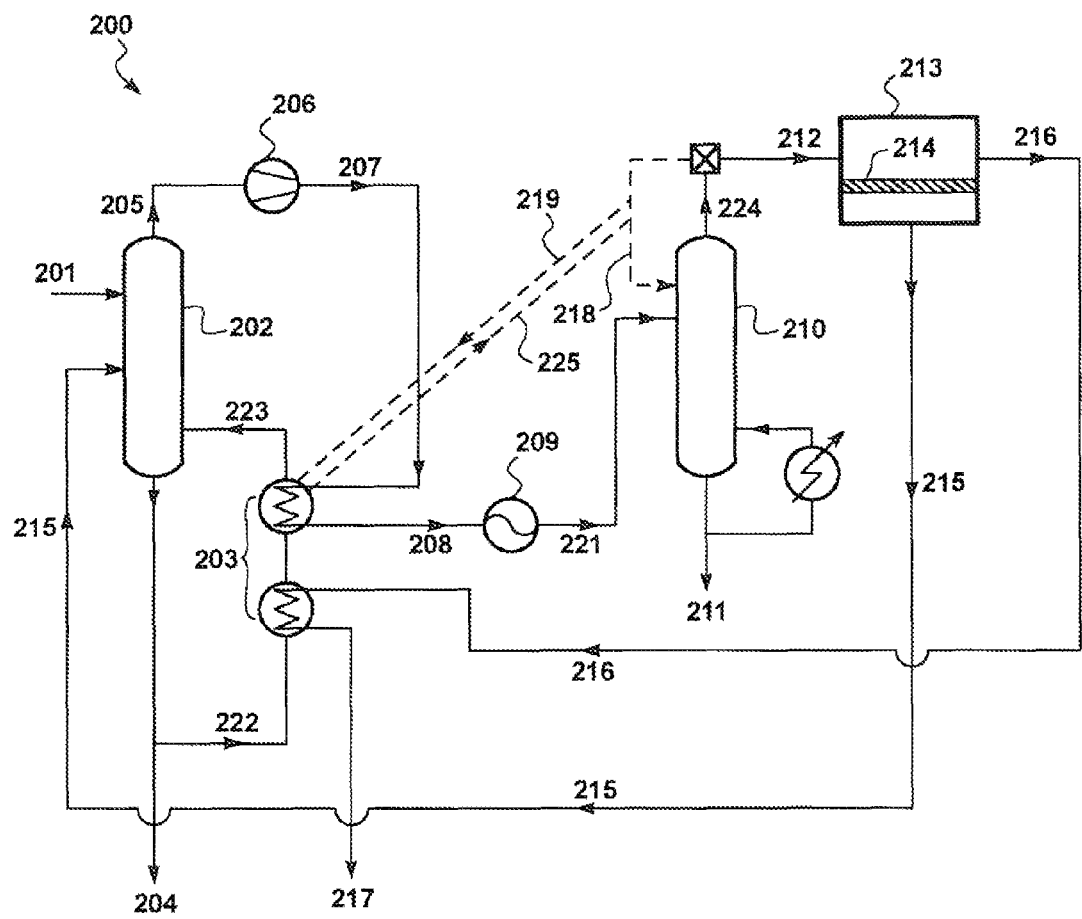
FIG. 2 is a schematic drawing showing the process flow scheme and apparatus elements for an embodiment of the invention which utilizes two distillation steps followed by a membrane separation step, and which involves recirculation of at least a portion of the membrane residue stream to the first reboiler system as a heating stream.

FIG. 2 is a schematic drawing, 200, showing the process flow scheme and apparatus elements for an embodiment of the invention which utilizes two distillation steps followed by a membrane separation step, and which involves recirculation of at least a portion of the membrane residue stream to the first reboiler as a heating stream. Unless explicitly specified otherwise, process conditions and membrane materials for this embodiment are the same as for the process embodiment illustrated schematically in FIG. 1.

Referring to FIG. 2, feed stream, 201, is passed into first distillation column, 202. Energy for the stripping column 202 is provided at least in part by reboiler heat exchanger, 203, in which a portion, 222, of the liquid bottoms stream, 204, is evaporated for return to the column as heated vapor stream, 223.

First overhead vapor stream, 205, is passed from the column to vapor compressor or compression step, 206. As discussed above, the compressor increases the pressure of the first overhead vapor stream about 1.5-fold, i.e., from 0.3-1.2 bar to about 0.45-1.8 bar.

The compressed overhead vapor stream, 207—enriched in solvent compared with raw feed 201—is condensed to produce condensed overhead stream, 208, then pumped through liquid feed pump, 209, as feed, 221, to the second distillation column, 210. Liquid feed pump 209 increases the pressure of the condensed overhead stream even further, to about 2-5 bar, as discussed above.

Stream 221 preferably enters second distillation column 210 at a position that matches its composition. The column produces a bottoms stream, 211, which may be sent to any destination.

Overhead vapor stream, 224, from column 210 passes as a feed stream, 212, to membrane separation step or unit, 213, containing membranes, 214, which may be of any type that provides selectivity in favor of water over the organic solvent, as discussed above.

Optionally, a portion, 219, of second overhead vapor stream 224 may be recirculated to the first reboiler system 203 as a heating stream, and a condensed liquid product 225 from the heat exchanger 203 is sent as a reflux liquid 218 to the second distillation step 210. At least a portion of second overhead vapor stream 224 may also be recirculated directly as reflux liquid 218 to the second distillation step 210.

Returning to the membrane separation step 213, water permeates the membranes 214 preferentially, to form water-enriched, solvent-depleted permeate stream, 215, which is withdrawn in vapor form and recirculated to the first distillation column 202. Stream 215 is preferably recirculated as a vapor to the lower part of column 202 without condensation, to recover its latent heat energy.

The residue stream, 216, from the membrane separation step 213—enriched in solvent compared with the feed stream 212—is recirculated to the reboiler heat exchanger 203 as a heating stream.

Optionally, the latent heat content of stream 216 can be used to raise the temperature of feed stream 201, which also lowers the reboiler duty of column 202.

At least a portion of residue stream 216 is withdrawn as a high-purity, dehydrated solvent product stream, 217, which preferably contains at least 90 wt % solvent, and more preferably, at least 95 wt % solvent. Most preferably, the product is dehydrated to at least 98 wt % or 99 wt % solvent, or better.

From the discussion above, it follows that energy is delivered to the reboiler system of the first column by condensing the overhead stream 207 (generally containing the largest amount of energy). But also, by condensing stream 216 and stream 219 from the second overhead column, it can be possible that the total amount of energy delivered to the reboiler in this way exceeds that required to operate column 201 as a simple stripper. In this case, operating the column as a rectifier with a few trays of separation above the feed point of stream 201, is beneficial. The liquid reflux required for this type of operation would be obtained by recirculating a portion of stream 208 to the top of column 202.

As mentioned above, if the raw feed to the process is very dilute, such as containing no more than about 5 wt % solvent, it is often convenient, and can result in lower overall energy usage, to use two membrane separation steps. FIG. 3 is a schematic drawing showing a preferred embodiment of the invention which utilizes two distillation steps followed by two sequential membrane separation steps, and which involves recirculation of the residue stream from the second membrane separation step to the first reboiler system as a heating stream.

Figure 3:
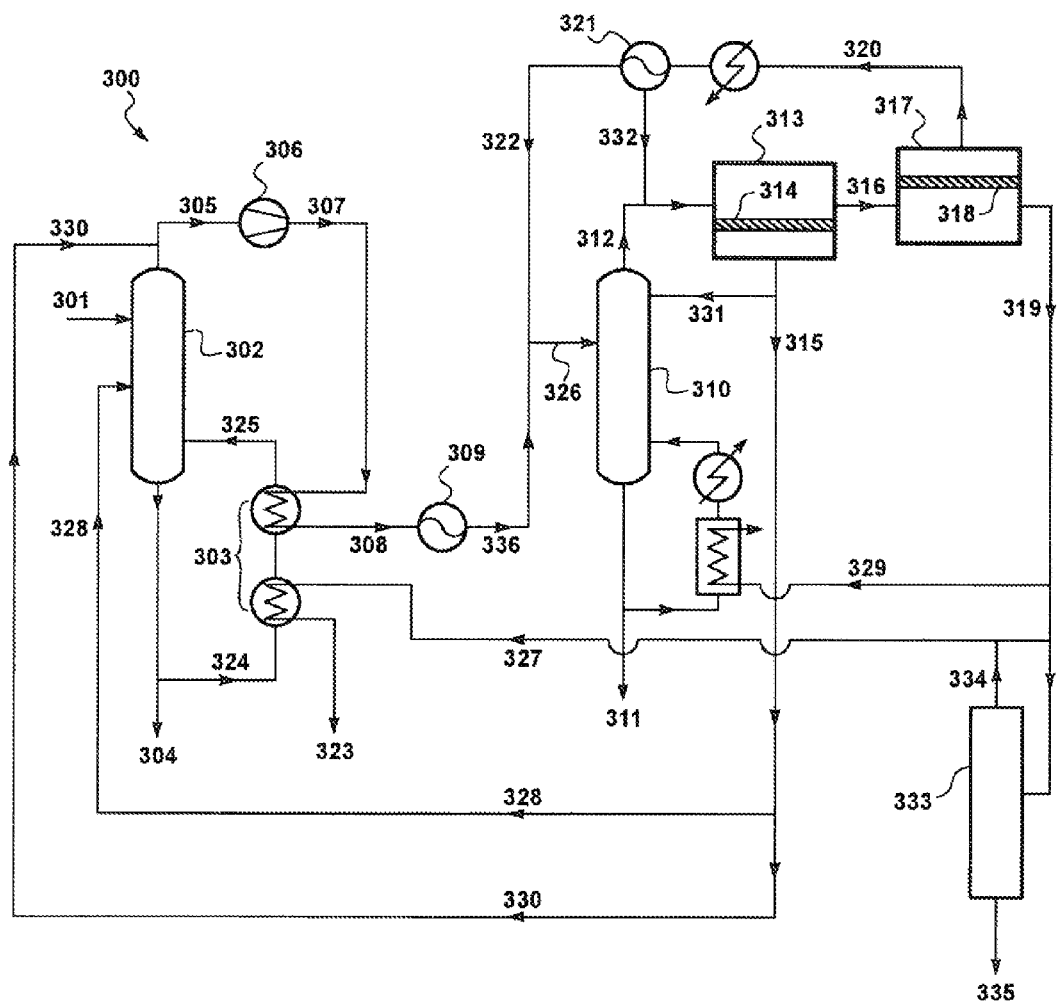
FIG. 3 is a schematic drawing showing a preferred embodiment of the invention which utilizes two distillation steps followed by two sequential membrane separation steps, and which involves recirculation of the residue stream from the second membrane separation step to the first reboiler system as a heating stream.

Unless explicitly specified otherwise, process conditions and membrane materials for the process embodiment of FIG. 3 are the same as those for FIG. 1.

Referring to FIG. 3, feed stream, 301, is passed into first distillation column, 302. Energy for the stripping column 302 is provided at least in part by reboiler heat exchanger, 303, in which a portion, 324, of the liquid bottoms stream, 304, is evaporated for return to the column as heated vapor stream, 325.

First overhead vapor stream, 305, is passed from the column to vapor compressor or compression step, 306. As discussed above with reference to the process embodiment illustrated in FIG. 1, the compressor increases the pressure of the first overhead vapor stream about 1.5-fold, i.e., from 0.3-1.2 bar to about 0.45-1.8 bar.

The compressed overhead vapor stream, 307—enriched in solvent compared with raw feed 301—is condensed to produce condensed overhead stream, 308, then pumped through liquid feed pump, 309. Stream, 336, exiting the liquid feed pump joins stream, 322 (discussed below), as feed, 326, to the second distillation column, 310. Liquid feed pump 309 increases the pressure of the condensed overhead stream even further, to about 2-5 bar, as discussed above.

Stream 326 preferably enters second distillation column 310 at a position that matches its composition. The column produces a bottoms stream, 311, which may be sent to any destination.

Overhead vapor stream, 312, from column 310 passes as a feed stream to a first membrane separation step or unit, 313, containing membranes, 314, which may be of any type that provides selectivity in favor of water over the organic solvent, as discussed above.

Water permeates the membranes 314 preferentially, to form water-enriched, solvent-depleted permeate stream, 315, which is withdrawn in vapor form and may be recirculated to the first distillation column 302. Stream 315 is preferably recirculated as a vapor stream, 328, to the lower part of column 302 without condensation, to recover its latent heat energy. Alternatively, stream 315 can be sent as stream, 330, back to first column overhead 305 prior to compression. In yet another alternative, stream 315 can be compressed (compressor not shown) and sent as stream, 331, back to second column 310. Each of these alternative dispositions for stream 315 is discussed further in the following Examples.

The residue stream, 316, from the first membrane separation step 313—enriched in solvent compared with the first membrane feed stream 312—is passed as a feed stream to a second membrane separation step or unit, 317, which contains membranes, 318, that have the same permeation properties as membranes 314 of first membrane separation unit 313. To achieve a better separation, the second membrane unit uses a condenser to reduce the pressure of the permeate to 0.1-0.2 bar, so the pressure ratio is 2-5 bar feed/0.1-0.2 bar permeate, i.e., 10-50.

Water permeates the membranes 318 preferentially, to form water-enriched, solvent-depleted permeate stream, 320, which is withdrawn in vapor form, optionally compressed in compressor, 321, then recirculated as compressed second permeate stream 322 to join stream 336 as feed 326 to the second distillation column 310. Alternatively, stream 320 may be compressed in compressor 321, then sent back to the process as stream, 332, after second column 310, but before first membrane unit 313. Each of these alternative dispositions for stream 320 is discussed further in the following Examples.

Alternatively, stream 322 could be mixed with incoming feed stream 301, or may be sent to some other portion of the process. Since this stream is small relative to the other recycle streams, 315 and 318, its final disposition will not significantly change the energy consumption of the process.

The residue stream, 319, from the second membrane separation step 317—enriched in solvent compared with the feed (first membrane residue) stream 316—is recirculated as re-heating stream, 327, to the reboiler heat exchanger 303, whence it is recirculated to first column 302 as a heating stream. Alternatively, stream 319 can be sent as heating stream, 329, back to second column 310. Each of these alternative dispositions for stream 319 is discussed further in the following Examples.

At least a portion of stream 327 is withdrawn as a high-purity, dehydrated solvent product stream, 323. Performing the solvent/water separation process with two sequential membrane separation steps—in accordance with the embodiment of the invention described above and shown schematically in FIG. 3—will typically yield a product stream containing at least 99 wt % solvent.

The invention is now further described by the following examples, which are intended to be illustrative of the invention, but are not intended to limit the scope or underlying principles in any way.

EXAMPLES

Example 1

Bases of Calculations for Examples

The computer calculations described in the following Examples were performed with a modeling program, ChemCad 6.0 (ChemStations, Inc., Houston, Tex.)—containing code developed by assignee's engineering group for applications specific to assignee's processes—to illustrate the process of the invention in the embodiment shown in FIG. 3, with various permutations, as will be described in each Example.

The calculation assumed that the feed composition was 0.75% ethanol and 99.25% water, representative of a raw feed from a bioethanol manufacturing process. The process was assumed to use two stripping columns having 20 stripping stages each. The columns were assumed to operate at 1.0 bar and 2.5 bar respectively.

The process was configured to provide a rectified overhead stream, 312, containing about 8 wt % ethanol, and a bottoms stream, 311, containing 0.02 wt % ethanol. The membranes were assumed to have a selectivity for water over ethanol of about 50-100 and a water permeance of about 1,000-3,000 gpu.

Example 2

Comparative Example-Single Distillation Column, Followed by Compression and Two Membrane Separation Steps (Not in Accordance with the Invention)

Figure 4:
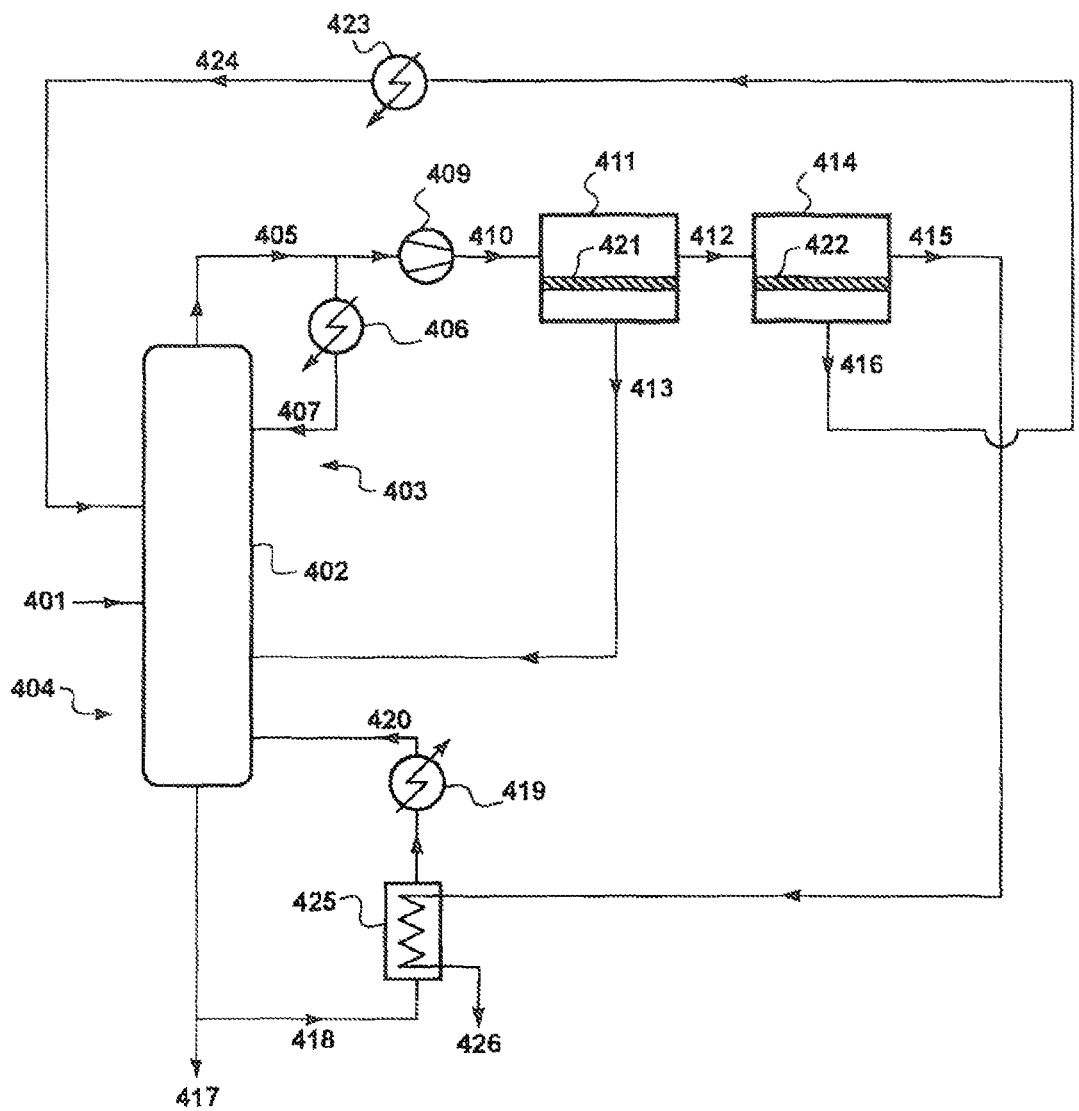
FIG. 4 is a schematic drawing showing a solvent dehydration process that includes a single distillation step, followed by a compression step and two membrane sequential membrane separation steps (not in accordance with the invention).

This calculation was performed according to the process schematic illustrated in FIG. 4, which uses a single distillation column. This process is described in U.S. Pat. No. 8,263,815.

According to this process, raw feed stream, 401, is passed into distillation column, 402. The column has an upper rectification section, 403, and a lower stripping section, 404. Cooling for the rectification section is provided at least in part by reflux condenser, 406, in which a portion of the overhead vapor stream, 405, is condensed for return to the column as reflux stream, 407.

Energy for the stripping section is provided at least in part by reboiler, 419, in which a portion, 418, of the liquid bottoms stream, 417, is boiled, typically by heating with steam, for return to the column as heated vapor stream, 420.

Rectified vapor stream, 405, is passed from the column to vapor compression step, 409. The compressed overhead vapor, 410, is introduced as a feed stream into the first membrane separation unit, 411, containing membranes, 421. First permeate stream, 413, is returned to the distillation column, 402.

The first residue stream, 412, is passed as feed in vapor form to the second membrane separation unit, 414, containing membranes, 422.

The second permeate stream, 416, is withdrawn as a vapor from the second membrane separation step and is passed through condenser, 423, where it is condensed to form liquid recycle stream, 424, which is returned to the rectification section of column 402, to form additional reflux for the column.

The second residue stream, 415, is withdrawn as a vapor from the second membrane separation step 414 and is passed through heat exchanger or step, 425, in heat-exchanging relationship with reboiler stream, 418. The resulting condensed product is withdrawn from the process as stream, 426:

First and second membranes, 421 and 422, were assumed to have areas of 4,300 $m^2$ and 5,000 $m^2$, respectively.

Results of the calculation are shown in Table 1.

TABLE 1

| | Parameter | | | | |
| --- | --- | --- | --- | --- | --- |
| | Total Flow | Temp. | Pressure | Component (mol %) | |
| Stream | (tons/h) | (° C.) | (bar) | Water | Ethanol |
| First Column Feed (401) | 1,000 | 30.3 | 2.0 | 99.7 | 0.3 |
| Bottoms Stream (420) | 993 | 81.2 | 0.5 | 100 | 0 |
| First Overhead Stream (405) | 39.7 | 79.0 | 0.5 | 90.3 | 9.7 |
| Compressed Overhead Stream (410) | 39.7 | 261 | 2.3 | 90.3 | 9.7 |
| First Membrane Feed (407) | 39.7 | 125 | 2.3 | 90.3 | 9.7 |
| First Membrane Residue (411) | 8.3 | 116 | 2.3 | 22.1 | 77.9 |
| First Membrane Permeate (413) | 31.4 | 120 | 0.5 | 98.7 | 1.3 |
| Second Membrane Residue (414) | 6.9 | 114 | 2.3 | 1.2 | 98.8 |
| Second Membrane Permeate (416) | 1.4 | 115 | 0.1 | 77.7 | 22.3 |
| Compressed Second Permeate (424) | 1.4 | 30.1 | 2.0 | 77.7 | 22.3 |

This process was calculated to use 228 million Btu/hour.

Example 3

Comparative Example-Stripping Column, Followed by a Dephiegamator and Two Membrane Separation Steps (Not in Accordance with the Invention)

Figure 5:
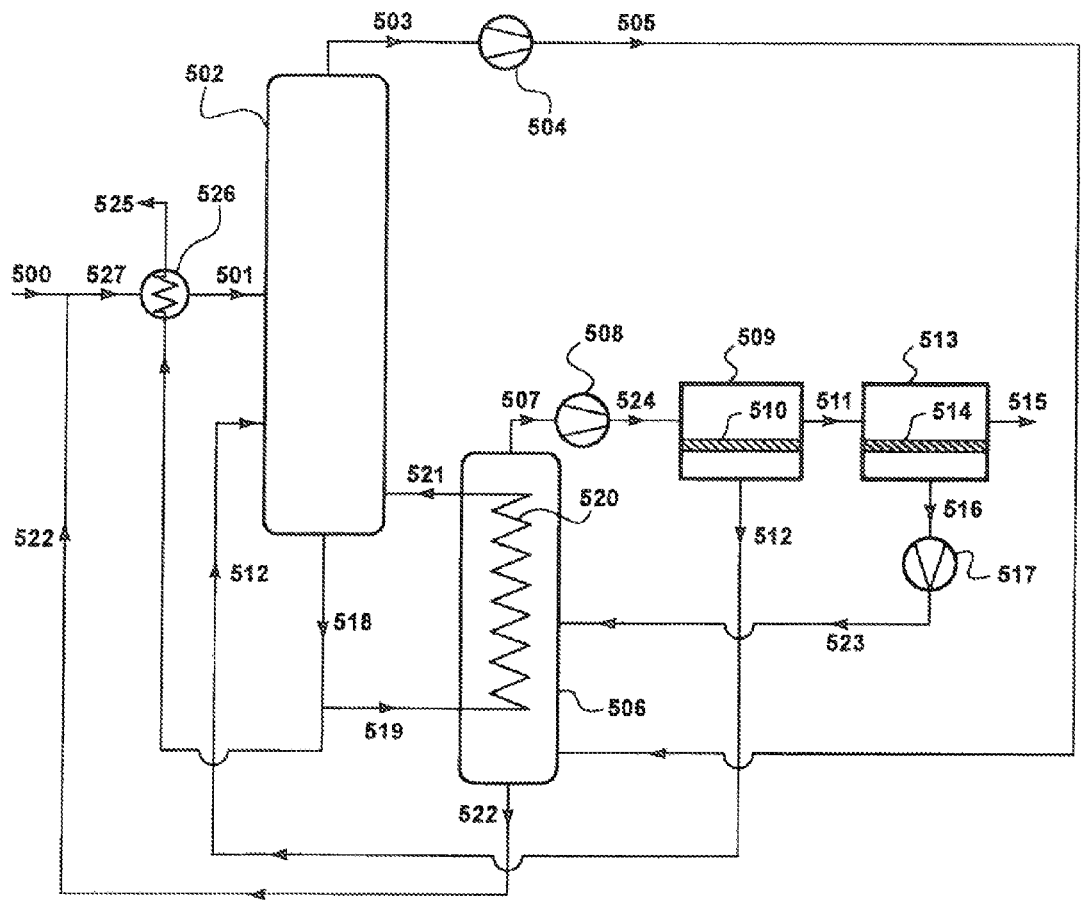
FIG. 5 is a schematic drawing showing a solvent dehydration process that includes a distillation step, followed by a dephlegmation step, a compression step, and two sequential membrane separation steps (not in accordance with the invention).

This calculation was performed according to the process schematic illustrated in FIG. 5, which uses a stripping column, followed by a compression step, followed by a dephlegmator. This process is described in U.S. Pat. No. 8,114,255.

According to this process, feed stream, 500, joins second column bottoms stream, 522 (discussed below), and passes as stream, 527, through heat exchanger, 526, where it joins first column bottoms stream, 518 (discussed below), as first column feed stream, 501, which passes into first distillation column, 502. Overhead stream, 503, is passed from the column to vapor compressor or compression step, 504. The compressed overhead vapor stream, 505, is passed as feed to the second column, 506. This column does not have an external reflux condenser, but rather takes the form of a simple shell-and-tube dephlegmator, with internal heat exchange, 520. Vapor 505 enters the column and flows upward on the shell side of the heat exchanger; reboil liquid stream, 519, from the first column flows in the tubes and passes out of the second column as heated reboil stream, 521.

Overhead vapor, 507, from the second column is compressed in compression step, 508, and passes as feed, 524, to membrane separation step or unit, 509, containing membranes, 510. This step separates the overhead stream into first residue stream, 511, and first permeate stream, 512. First permeate stream is returned to the bottom of first column 502.

First residue stream 511 is withdrawn from membrane unit 509 and passed as feed in vapor form to the second membrane separation unit, 513, containing membranes, 514. This unit produces a second residue stream, 515, which is the dehydrated product of the process, and a second permeate stream, 516.

Second permeate stream 516 is recycled through vacuum pump, 517, and passed as compressed stream, 523, back to second column 506.

Second column bottoms streams, 522, is withdrawn and joins feed stream, 500, and passes as stream, 527, through heat exchanger, 526, where it joins first column bottoms stream, 518 (discussed below), as first column feed stream, 501, which passes into first distillation column, 502. Product-depleted stream, 525, is withdrawn as a vent stream.

First and second membranes, 510 and 514, were assumed to have areas of 2,700 m$^2$ and 3,200 m$^2$, respectively.

Results of the calculation are shown in Table 2.

TABLE 2

| Stream | Parameter | | | | |
|---|---|---|---|---|---|
| | Total Flow (tons/h) | Temp. (° C.) | Pressure (bar) | Component (wt %) | |
| | | | | Water | Ethanol |
| Process Feed (500) | 1,000 | 37 | 1.0 | 99.25 | 0.75 |
| First Column Feed (501) | 1,098 | 90.4 | 1.0 | 99.24 | 0.76 |
| First Bottoms Stream (518) | 993 | 99.6 | 1.0 | 100 | 0 |
| First Overhead Stream (503) | 112 | 98.7 | 1.0 | 91.4 | 8.6 |
| Feed to Second Column (505) | 112 | 155 | 1.8 | 91.4 | 8.6 |
| Second Bottoms Stream (522) | 97.7 | 116 | 1.8 | 99.1 | 0.9 |
| Second Overhead Stream (507) | 15.5 | 105 | 1.8 | 40.0 | 60.0 |
| First Membrane Feed (524) | 15.5 | 124 | 3.0 | 40.0 | 60.0 |
| First Membrane Residue (511) | 8.7 | 119 | 3.0 | 10.0 | 90.0 |
| First Membrane Permeate (512) | 6.8 | 121 | 1.0 | 78.0 | 22.0 |
| Second Membrane Residue (515) | 7.3 | 117 | 3.0 | 0.5 | 99.5 |
| Second Membrane Permeate (516) | 1.3 | 118 | 0.1 | 62.6 | 37.4 |
| Compressed Second Permeate (523) | 1.3 | 30.0 | 1.8 | 62.6 | 37.4 |

This process was calculated to use 74 million Btu/hour.

Example 4

Comparative Example-Two Distillation Columns, Followed by Two Membrane Separation Steps, with No Compression (Not in Accordance with the Invention)

Figure 6:
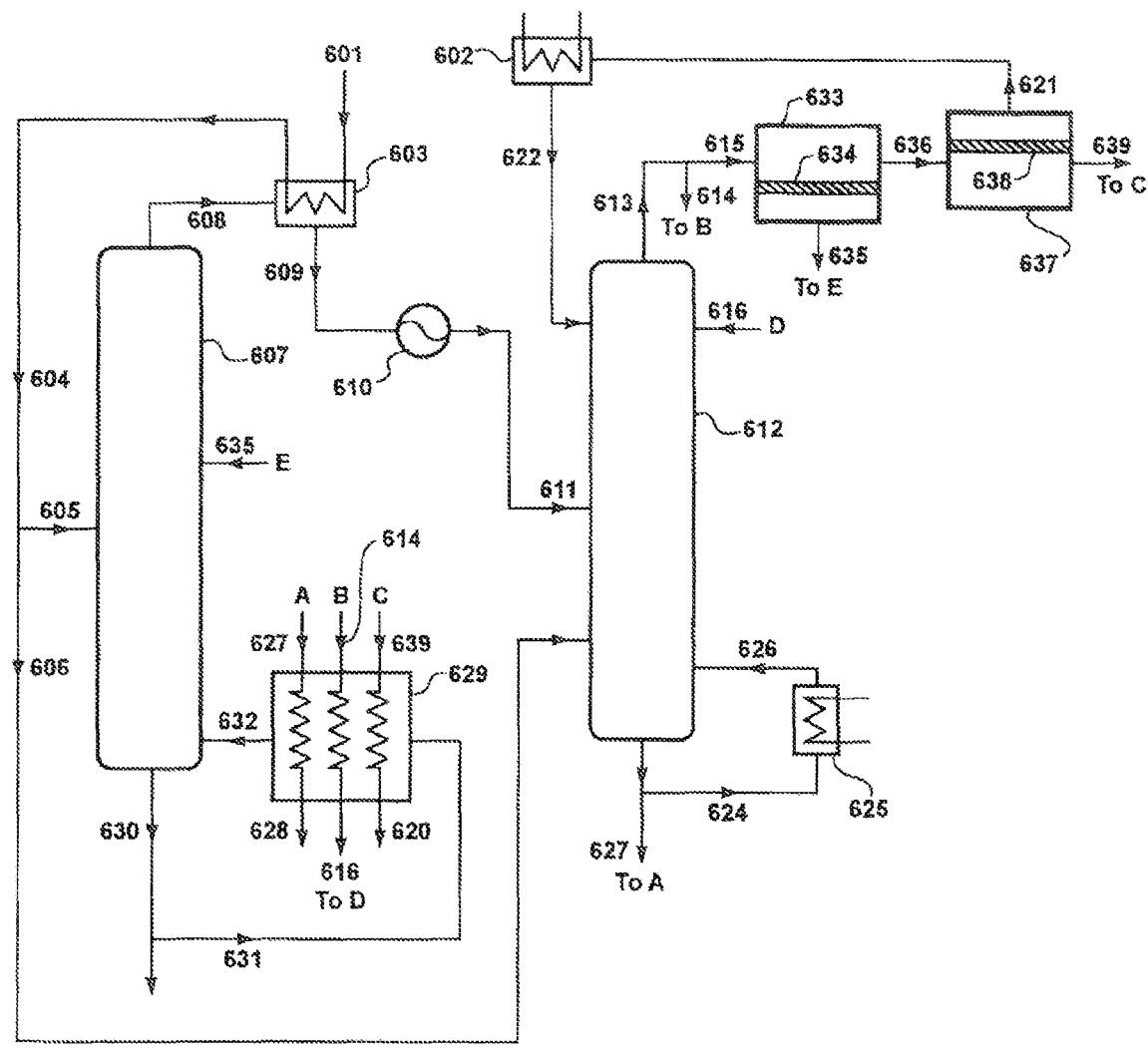
FIG. 6 is a schematic drawing showing a solvent dehydration process that includes two sequential distillation steps, followed by two membrane separation steps, with no compression (not in accordance with the invention).

This calculation was performed according to the process schematic illustrated in FIG. 6. This process is described in U.S. Pat. No. 8,128,787.

According to this process, raw feed stream, 601, enters the process and is warmed by heat exchange against first overhead vapor stream, 608, in heat exchanger/condenser, 603.

Warmed feed, 604, is split into two portions, 605 and 606. Stream 605 passes into first distillation column, 607. Energy for operating this column is provided at least in part by first reboiler/heat exchanger system, 629, in which a portion, 631, of the liquid bottoms stream, 630, is evaporated for return to the column as heated vapor stream, 632.

In this case, three streams from within the process supply heat to the reboiler system: stream 627, the bottoms stream from the second column, which is passed into the heat exchanger as shown at A; stream 614, the reflux stream for the second column, which is passed into the heat exchanger as shown at B; and stream 639, the residue product stream, which is passed into the heat exchanger as shown at C.

First overhead vapor stream, 608, is passed from column 607 to condensation step or condenser, 603, and the condensate stream, 609, is pumped by liquid pump, 610, under pressure as liquid, 611, to the second distillation column, 612. The second portion, 606, of the raw feed also enters the second column.

Condensed reflux liquid from first column 607, stream 616, returns from the first reboiler system 629 to the second column 612, as shown at D.

Second column 612 has a reboiler system, 625, through which a portion, 624, of bottoms stream, 627, is passed for return as hot vapor reboil stream, 626. The remainder of bottoms stream 627 is passed as stream A to first reboiler system 629 for heat recovery, as described above, and is discharged from the process as cooled stream, 628.

The portion, 615, of second overhead vapor stream, 613, that is not sent for reflux is passed as a feed stream to a first membrane separation step, 633, which uses membranes, 634, to separate the stream into residue stream, 636, and permeate stream, 635.

The permeate stream 635 is returned as vapor to the first column, as shown at E. The residue stream 636 passes as feed to the second membrane separation step, 637, using membranes, 638. The permeate from this step passes as stream 621 to condenser 602. The second residue stream, 639, is the product of the process, and is condensed in reboiler system 629 to form liquid product stream, 620.

First and second membranes, 634 and 638, were assumed to have areas of 2,100 m$^2$ and 4,300 m$^2$, respectively.

Results of the calculation are shown in Table 3.

TABLE 3

| Stream | Parameter | | | | |
|---|---|---|---|---|---|
| | Total Flow (tons/h) | Temp. (° C.) | Pressure (bar) | Component (wt %) | |
| | | | | Water | Ethanol |
| Process Feed (601) | 1,000 | 37 | 1.0 | 99.25 | 0.75 |
| First Column Feed | 630 | 75.7 | 1.0 | 99.25 | 0.75 |

TABLE 3-continued

| Stream | Total Flow (tons/h) | Temp. (° C.) | Pressure (bar) | Component (wt %) Water | Component (wt %) Ethanol |
|---|---|---|---|---|---|
| (605) | | | | | |
| First Bottoms Stream (630) | 576 | 81.3 | 0.5 | 100 | 0 |
| First Overhead Stream (608) | 67.5 | 80.5 | 0.5 | 92.0 | 8.0 |
| Condensed Overhead Stream (609) | 67.5 | 42.0 | 0.5 | 92.0 | 8.0 |
| Feed to Column Two (611) | 67.5 | 60.0 | 2.5 | 92.0 | 8.0 |
| Feed to Column Two (606) | 370 | 80.1 | 2.5 | 99.25 | 0.75 |
| Second Bottoms Stream (627) | 417 | 127 | 2.5 | 99.9 | 0.1 |
| First Membrane Feed (615) | 21.5 | 124 | 2.5 | 61.4 | 38.6 |
| First Membrane Residue (636) | 8.3 | 117 | 2.5 | 9.9 | 90.1 |
| First Membrane Permeate (635) | 13.2 | 121 | 0.5 | 94.0 | 6.0 |
| Second Membrane Residue (639) | 7.0 | 115 | 2.5 | 0.5 | 99.5 |
| Second Membrane Permeate (621) | 1.3 | 116 | 0.1 | 59.2 | 40.8 |
| Compressed Second Permeate (622) | 1.3 | 29.1 | 2.5 | 59.2 | 40.8 |

This process was calculated to use 172 million Btu/hour.

Although the process designs shown in FIGS. 4, 5, and 6, and described in Examples 2, 3, and 4, work well for higher concentrations of ethanol, for concentrations of ethanol less than about 5 wt %, they require too much energy input to be efficient and economical.

Example 5

No Heat Integration

This calculation was performed according to the process schematic illustrated in FIG. 3, but with no heat integration (i.e., just a series of unit operations with no heat integration). First and second membranes, 314 and 318, were assumed to have areas of 6,000 m² and 11,000 m², respectively.

Results of the calculation are shown in Table 4.

TABLE 4

| Stream | Total Flow (tons/h) | Temp. (° C.) | Pressure (bar) | Component (wt %) Water | Component (wt %) Ethanol |
|---|---|---|---|---|---|
| First Column Feed (301) | 1,000 | 97 | 1.1 | 99.25 | 0.75 |
| First Bottoms Stream (304) | 898 | 102 | 1.1 | 100 | 0 |
| First Overhead Stream (305) | 102 | 101 | 1.1 | 92.8 | 7.2 |
| Compressed Overhead Stream (307) | 102 | 154 | 1.7 | 92.8 | 7.2 |
| Condensed Stream (308) | 102 | 30 | 1.7 | 92.8 | 7.2 |
| Second Column Feed (326) | 118 | 109 | 2.5 | 90.7 | 9.3 |
| Second Bottoms Stream (311) | 94.4 | 128 | 2.5 | 99.9 | 0.1 |

TABLE 4-continued

| Stream | Total Flow (tons/h) | Temp. (° C.) | Pressure (bar) | Component (wt %) Water | Component (wt %) Ethanol |
|---|---|---|---|---|---|
| First Membrane Feed (312) | 23.8 | 123 | 2.5 | 54.2 | 45.8 |
| First Membrane Residue (316) | 10.0 | 118 | 2.5 | 13.9 | 86.1 |
| First Membrane Permeate (315) | 13.8 | 121 | 1.1 | 83.4 | 16.6 |
| Second Membrane Residue (319) | 7.3 | 115 | 2.5 | 0.4 | 99.6 |
| Second Membrane Permeate (320) | 2.7 | 117 | 0.2 | 49.5 | 50.5 |
| Compressed Second Permeate (322) | 2.7 | 42.5 | 2.5 | 49.5 | 50.5 |

This process—which was just a series of unit operations with no heat integration—was calculated to use 81.2 million Btu/hour.

Example 6

Maximum Heat Integration

This calculation was performed according to the process schematic illustrated in FIG. 3, with first membrane permeate 315 sent as stream 328 back to first column 302, and ethanol-rich second membrane residue 319 sent as re-heating stream, 327, back to reboiler 303. First and second membranes, 314 and 318, were assumed to have areas of 3,000 m² and 8,000 m², respectively.

Results of the calculation are shown in Table 5.

TABLE 5

| Stream | Total Flow (tons/h) | Temp. (° C.) | Pressure (bar) | Component (wt %) Water | Component (wt %) Ethanol |
|---|---|---|---|---|---|
| First Column Feed (301) | 1,000 | 101 | 1.1 | 99.25 | 0.75 |
| First Bottoms Stream (304) | 929 | 102 | 1.1 | 100 | 0 |
| First Overhead Stream (305) | 134 | 101 | 1.1 | 89.2 | 10.8 |
| Compressed Overhead Stream (307) | 134 | 147 | 1.6 | 89.2 | 10.8 |
| Condensed Stream (308) | 80.4 | 30 | 1.6 | 89.2 | 10.8 |
| Second Column Feed (326) | 82.9 | 108 | 2.8 | 88.2 | 11.8 |
| Second Bottoms Stream (311) | 64.2 | 131 | 2.8 | 99.9 | 0.1 |
| First Membrane Feed (312) | 18.8 | 125 | 2.8 | 48.2 | 51.8 |
| First Membrane Residue (316) | 9.8 | 120 | 2.8 | 14.8 | 85.2 |
| First Membrane Permeate (328) | 8.9 | 122 | 1.1 | 84.9 | 15.1 |
| Second Membrane Residue (319) | 7.3 | 107 | 2.8 | 0.5 | 99.5 |
| Second Membrane Permeate (320) | 2.6 | 119 | 0.2 | 55.9 | 44.1 |
| Compressed Second Permeate (322) | 2.6 | 42.9 | 2.8 | 55.9 | 44.1 |

This process was calculated to use 64 million Btu/hour.

Example 7

First Membrane Permeate Sent Back to First Column, and Second Membrane Residue Sent Back to Second Column This calculation was performed according to the process schematic illustrated in FIG. 3, with first membrane permeate 315 sent as stream 328 back to first column 302, and ethanol-rich second membrane residue 319 sent as stream 329 as a heating stream back to second column 310 via a compressor.

First and second membranes, 314 and 318, were assumed to have areas of 3,000 m² and 11,000 m², respectively.

Results of the calculation are shown in Table 6.

TABLE 6

| | Parameter | | | | |
|---|---|---|---|---|---|
| | Total Flow | Temp. | Pressure | Component (wt %) | |
| Stream | (tons/h) | (° C.) | (bar) | Water | Ethanol |
| First Column Feed (301) | 1,000 | 97.6 | 1.1 | 99.25 | 0.75 |
| First Bottoms Stream (304) | 896 | 102 | 1.1 | 100 | 0 |
| First Overhead Stream (305) | 115 | 101 | 1.1 | 92.9 | 7.1 |
| Compressed Overhead Stream (307) | 115 | 151 | 1.6 | 92.9 | 7.1 |
| Condensed Stream (308) | 115 | 30 | 1.6 | 92.9 | 7.1 |
| Second Column Feed (326) | 119 | 110 | 2.5 | 92.0 | 8.0 |
| Second Bottoms Stream (311) | 96.9 | 128 | 2.5 | 99.9 | 0.1 |
| First Membrane Feed (312) | 22.5 | 124 | 2.5 | 57.7 | 42.3 |
| First Membrane Residue (316) | 11.3 | 120 | 2.5 | 23.8 | 76.2 |
| First Membrane Permeate (328) | 11.2 | 122 | 1.1 | 91.8 | 8.2 |
| Second Membrane Residue (329) | 7.3 | 130 | 5.8 | 0.5 | 99.5 |
| Second Membrane Permeate (320) | 4.0 | 118 | 0.2 | 66.1 | 33.9 |
| Compressed Second Permeate (322) | 4.0 | 43.8 | 2.5 | 66.1 | 33.9 |

This process was calculated to use 70.8 million Btu/hour.

Example 8

First Membrane Permeate Sent Back to First Column Overhead, and Second Membrane Residue Sent to Second Column This calculation was performed according to the process schematic illustrated in FIG. 3, with first membrane permeate 315 sent as stream 330 back to first column overhead 305 prior to compression, and ethanol-rich second membrane residue 319 sent as stream 329 as a heating stream back to second column 310 via a compressor.

First and second membranes, 314 and 318, were assumed to have areas of 3,000 m² and 11,000 m², respectively.

Results of the calculation are shown in Table 7.

TABLE 7

| | Parameter | | | | |
|---|---|---|---|---|---|
| | Total Flow | Temp. | Pressure | Component (wt %) | |
| Stream | (tons/h) | (° C.) | (bar) | Water | Ethanol |
| First Column Feed (301) | 1,000 | 97.4 | 1.1 | 99.25 | 0.75 |
| First Bottoms Stream (304) | 898 | 102 | 1.1 | 100 | 0 |
| First Overhead Stream (305) | 102 | 101 | 1.1 | 92.8 | 7.2 |
| Compressed Overhead Stream (307) | 113 | 153 | 1.6 | 92.7 | 7.3 |
| Condensed Stream (308) | 113 | 30 | 1.6 | 92.7 | 7.3 |
| Second Column Feed (326) | 117 | 110 | 2.5 | 91.8 | 8.2 |
| Second Bottoms Stream (311) | 94.5 | 128 | 2.5 | 99.9 | 0.1 |
| First Membrane Feed (312) | 22.2 | 124 | 2.5 | 57.2 | 42.8 |
| First Membrane Residue (316) | 11.2 | 120 | 2.5 | 23.5 | 76.5 |
| First Membrane Permeate (330) | 11.0 | 122 | 1.1 | 91.6 | 8.4 |
| Second Membrane Residue (329) | 7.3 | 130 | 5.8 | 0.5 | 99.5 |
| Second Membrane Permeate (320) | 4.0 | 118 | 0.2 | 65.8 | 34.2 |
| Compressed Second Permeate (322) | 4.0 | 43.8 | 2.5 | 65.8 | 34.2 |

This process was calculated to use 69.5 million Btu/hour.

Example 9

First Membrane Permeate Compressed and Sent Back to Second Column, and Second Membrane Residue Sent Back to First Column This calculation was performed according to the process schematic illustrated in FIG. 3, with first membrane permeate 315 compressed (compressor not shown) and sent as stream 331 back to second column 310, and ethanol-rich second membrane residue 319 sent as re-heating stream, 327, back to first column 302.

First and second membranes, 314 and 318, were assumed to have areas of 6,000 m² and 11,000 m², respectively.

Results of the calculation are shown in Table 8.

TABLE 8

| | Parameter | | | | |
|---|---|---|---|---|---|
| | Total Flow | Temp. | Pressure | Component (wt %) | |
| Stream | (tons/h) | (° C.) | (bar) | Water | Ethanol |
| First Column Feed (301) | 1,000 | 99.2 | 1.1 | 99.25 | 0.75 |
| First Bottoms Stream (304) | 896 | 102 | 1.1 | 100 | 0 |
| First Overhead Stream (305) | 104 | 101 | 1.1 | 93.0 | 7.0 |
| Compressed Overhead Stream (307) | 104 | 151 | 1.6 | 93.0 | 7.0 |
| Condensed Stream (308) | 104 | 30 | 1.6 | 93.0 | 7.0 |
| Second Column Feed (326) | 107 | 65 | 2.5 | 91.9 | 8.1 |

TABLE 8-continued

| Stream | Total Flow (tons/h) | Temp. (°C.) | Pressure (bar) | Component (wt %) Water | Component (wt %) Ethanol |
|---|---|---|---|---|---|
| Second Bottoms Stream (311) | 97.1 | 128 | 2.5 | 99.9 | 0.1 |
| First Membrane Feed (312) | 28.0 | 125 | 2.5 | 62.8 | 38.2 |
| First Membrane Residue (316) | 10.2 | 119 | 2.5 | 15.3 | 84.7 |
| First Membrane Permeate (315) | 17.8 | 122 | 1.1 | 88.3 | 11.7 |
| Compressed First Permeate (331) | 17.8 | 235 | 2.5 | 88.3 | 11.7 |
| Second Membrane Residue (327) | 7.3 | 116 | 2.5 | 0.4 | 99.6 |
| Second Membrane Permeate (320) | 2.9 | 118 | 0.2 | 52.5 | 47.5 |
| Compressed Second Permeate (322) | 2.9 | 118 | 2.5 | 52.5 | 47.5 |

This process was calculated to use 68.5 million Btu/hour.

Example 10

First Membrane Permeate Compressed and Sent Back to Second Column, Second Membrane Residue Sent Back to First Column, and Second Membrane Permeate Compressed and Sent Back to Process after Second Column, but Before First Membrane Unit This calculation was performed according to the process schematic illustrated in FIG. 3, with first membrane permeate 315 compressed (compressor not shown) and sent as stream 331 back to second column 310, ethanol-rich second membrane residue 319 sent as re-heating stream, 327, back to first column 302, and second membrane permeate 320 compressed and sent as stream 332 after second column 310, but before first membrane unit 313.

First and second membranes, 314 and 318, were assumed to have areas of 6,000 m² and 11,000 m², respectively.

Results of the calculation are shown in Table 9.

TABLE 9

| Stream | Total Flow (tons/h) | Temp. (°C.) | Pressure (bar) | Component (wt %) Water | Component (wt %) Ethanol |
|---|---|---|---|---|---|
| First Column Feed (301) | 1,000 | 99.2 | 1.1 | 99.25 | 0.75 |
| First Bottoms Stream (304) | 896 | 102 | 1.1 | 100 | 0 |
| First Overhead Stream (305) | 104 | 101 | 1.1 | 93.0 | 7.0 |
| Compressed Overhead Stream (307) | 104 | 151 | 1.6 | 93.0 | 7.0 |
| Condensed Stream (308) | 104 | 30 | 1.6 | 93.0 | 7.0 |
| Second Column Feed (326) | 104 | 65 | 2.5 | 93.0 | 7.0 |
| Second Bottoms Stream (311) | 97.1 | 128 | 2.5 | 99.9 | 0.1 |
| First Membrane Feed (312) | 35.4 | 127 | 2.5 | 70.9 | 29.1 |

TABLE 9-continued

| Stream | Total Flow (tons/h) | Temp. (°C.) | Pressure (bar) | Component (wt %) Water | Component (wt %) Ethanol |
|---|---|---|---|---|---|
| First Membrane Residue (316) | 10.5 | 121 | 2.5 | 18.4 | 81.6 |
| First Membrane Permeate (315) | 24.8 | 124 | 1.1 | 93.1 | 6.9 |
| Compressed First Permeate (331) | 24.8 | 241 | 2.5 | 93.1 | 6.9 |
| Second Membrane Residue (319) | 7.3 | 117 | 2.5 | 0.5 | 99.5 |
| Second Membrane Permeate (320) | 3.3 | 119 | 0.2 | 58.1 | 41.9 |
| Compressed Second Permeate (332) | 3.3 | 402 | 2.5 | 58.1 | 41.9 |

This process was calculated to use 71.9 million Btu/hour.

Example 11

Maximum Heat Integration, with Molecular Sieving After Second Membrane Separation Step This calculation was performed according to the process schematic illustrated in FIG. 3, with first membrane permeate 315 sent as stream 328 back to first column 302. This calculation is similar to the calculation in Example 6, but in this case, ethanol-rich second membrane residue 319 is sent through a molecular sieve dryer, 333, prior to being passed as re-heating stream, 334, back to reboiler 303. This reduced the required membrane area of the second membrane 318 to 2,666 m². The first membrane 314 was assumed to have an area of 3,000 m².

Results of the calculation are shown in Table 10.

TABLE 10

| Stream | Total Flow (tons/h) | Temp. (°C.) | Pressure (bar) | Component (wt %) Water | Component (wt %) Ethanol |
|---|---|---|---|---|---|
| First Column Feed (301) | 1,000 | 101 | 1.1 | 99.25 | 0.75 |
| First Bottoms Stream (304) | 928 | 102 | 1.1 | 100 | 0 |
| First Overhead Stream (305) | 134 | 101 | 1.1 | 89.2 | 10.8 |
| Compressed Overhead Stream (307) | 134 | 147 | 1.6 | 89.2 | 10.8 |
| Condensed Stream (308) | 80 | 30 | 1.6 | 89.2 | 10.8 |
| Second Column Feed (326) | 84 | 107 | 2.8 | 89.2 | 10.8 |
| Second Bottoms Stream (311) | 64 | 131 | 2.8 | 99.9 | 0.1 |
| First Membrane Feed (312) | 19.7 | 124 | 2.8 | 46.5 | 53.5 |
| First Membrane Residue (316) | 10.9 | 120 | 2.8 | 15.4 | 84.6 |
| First Membrane Permeate (328) | 8.8 | 122 | 1.1 | 84.7 | 15.3 |
| Second Membrane Residue (319) | 9.1 | 118 | 2.8 | 2.6 | 97.4 |
| Second Membrane Permeate (320) | 1.8 | 119 | 0.2 | 80.3 | 19.7 |
| Condensed Second Permeate (322) | 1.8 | 46 | 2.8 | 80.3 | 19.7 |

TABLE 10-continued

| Stream | Parameter | | | | |
|---|---|---|---|---|---|
| | Total Flow (tons/h) | Temp. (°C.) | Pressure (bar) | Component (wt %) Water | Component (wt %) Ethanol |
| Molecular Sieve Stream (334) | 7.3 | 118 | 2.8 | 0.5 | 99.5 |
| Molecular Sieve Residue (335) | 1.8 | 118 | 2.8 | 11.4 | 88.6 |

This process was calculated to use 61.3 million Btu/hour.

We claim:

1. A process for recovering an organic solvent from a solvent and water mixture, comprising:
   (a) subjecting at least a first portion of the mixture to a first distillation step, carried out by passing a first feed stream of the mixture, at a first pressure, into a first distillation column having a first reboiler system which includes a heat exchanger, to produce a solvent-enriched, first overhead vapor stream and a first bottoms stream, wherein the first bottoms stream is enriched in water compared with the first feed stream;
   (b) compressing at least a portion of the first overhead vapor stream to form a compressed overhead vapor stream;
   (c) recovering heat by passing at least a portion of the compressed overhead vapor stream through the first reboiler system as a heating stream;
   (d) condensing at least a portion of the compressed overhead vapor stream to form a condensed overhead stream;
   (e) pumping at least a portion of the condensed overhead stream to a second distillation step, carried out under a second pressure that is higher than the first pressure in a second distillation column having a second reboiler system, to produce a solvent-enriched, second overhead vapor stream and a second bottoms stream, wherein the second bottoms stream is enriched in water compared with the condensed overhead stream; and
   (f) performing a membrane separation step, comprising:
      (i) providing a membrane having a feed side and a permeate side, the membrane being selective in favor of water over solvent;
      (ii) passing at least a portion of the second overhead vapor stream at a feed pressure across the feed side;
      (iii) maintaining a permeate pressure on the permeate side that is lower than the feed pressure;
      (iv) withdrawing from the feed side, as a residue stream, a dehydrated product stream; and
      (v) withdrawing from the permeate side a permeate stream enriched in water compared with the second overhead vapor stream.

2. The process of claim 1, wherein the first pressure is within the range of about 0.3 bar to about 1.2 bar.

3. The process of claim 1, wherein the first overhead vapor stream is compressed to a pressure that is great enough to raise the dew point sufficiently that the first overhead vapor stream can be condensed in the first reboiler system.

4. The process of claim 1, wherein the second pressure is within the range of about 2 bar to about 5 bar.

5. The process of claim 1, wherein the solvent comprises ethanol.

6. The process of claim 5, wherein the membrane has a selectivity in favor of water over ethanol within the range of about 20 to about 200.

7. The process of claim 1, wherein the permeate stream is recirculated to the first distillation step.

8. The process of claim 7, wherein the permeate stream is recirculated to the first distillation step without condensation.

9. The process of claim 7, wherein the permeate stream is compressed before being recirculated to the first distillation step.

10. A process for recovering an organic solvent from a solvent and water mixture, comprising:
   (a) subjecting at least a first portion of the mixture to a first distillation step, carried out by passing a first feed stream of the mixture, at a first pressure, into a first distillation column having a first reboiler system which includes a first heat exchanger, to produce a solvent enriched, first overhead vapor stream and a first bottoms stream, wherein the first bottoms stream is enriched in water compared with the first feed stream;
   (b) compressing at least a portion of the first overhead vapor stream to form a compressed overhead vapor stream;
   (c) recovering heat by passing at least a portion of the compressed overhead vapor stream through the first reboiler system as a heating stream;
   (d) condensing at least a portion of the compressed overhead vapor stream to form a condensed overhead stream;
   (e) pumping at least a portion of the condensed overhead stream to a second distillation step, carried out under a second pressure that is higher than the first pressure in a second distillation column having a second reboiler system and a reflux condenser system, to produce a solvent-enriched, second overhead vapor stream and a second bottoms stream, wherein the second bottoms stream is enriched in water compared with the condensed overhead stream;
   (f) performing a membrane separation step, comprising:
      (i) providing a membrane having a feed side and a permeate side, the membrane being selective in favor of water over solvent;
      (ii) passing at least a portion of the second overhead vapor stream at a feed pressure across the feed side;
      (iii) maintaining a permeate pressure on the permeate side that is lower than the feed pressure;
      (iv) withdrawing from the feed side, as a residue stream, a dehydrated product stream; and
      (v) withdrawing from the permeate side a permeate stream enriched in water compared with the second overhead vapor stream;
   (g) recirculating at least a portion of one or more of the permeate stream to the first distillation step, or the residue stream to the first reboiler system as a heating stream; and
   (h) condensing and withdrawing at least a portion of the residue stream as a high-purity solvent stream.

11. The process of claim 10, wherein the first pressure is within the range of about 0.3 bar to about 1.2 bar.

12. The process of claim 10, wherein the first overhead vapor stream is compressed to a pressure that is great enough to raise the dew point sufficiently that the first overhead vapor stream can be condensed in the first reboiler system.

13. The process of claim 10, wherein the second pressure is within the range of about 2 bar to about 5 bar.

14. The process of claim 10, wherein the solvent comprises ethanol.

15. The process of claim 14, wherein the membrane has a selectivity in favor of water over ethanol within the range of about 20 to about 200.

16. The process of claim 10, wherein at least a portion of the second overhead vapor stream is recirculated to the first reboiler system as a heating stream, and wherein a condensed liquid product from the heat exchanger is sent as a reflux liquid to the second distillation step.

17. The process of claim 10, wherein at least a portion of the second overhead vapor stream is recirculated to the second distillation step.

18. The process of claim 17, wherein the at least a portion of the second overhead vapor stream is compressed before being recirculated to the second distillation step.

19. The process of claim 10, wherein step (g) comprises recirculating at least a portion of the permeate stream to the first distillation step without condensation.

20. A process for recovering an organic solvent from a solvent and water mixture, comprising;
  (a) subjecting at least a first portion of the mixture to a first distillation step, carried out by passing a first feed stream of the mixture, at a first pressure, into a first distillation column having a first reboiler system which includes a first heat exchanger, to produce a solvent-enriched, first overhead vapor stream and a first bottoms stream, wherein the first bottoms stream is enriched in water compared with the first feed stream;
  (b) recirculating at least a portion of the first bottoms stream to the first distillation step;
  (c) compressing at least a portion of the first overhead vapor stream to form a compressed overhead vapor stream;
  (d) recovering heat by passing at least a portion of the compressed overhead vapor stream through the first reboiler system as a heating stream;
  (e) condensing at least a portion of the compressed overhead vapor stream to form a condensed overhead stream;
  (f) pumping at least a portion of the condensed overhead stream to a second distillation step, carried out under a second pressure that is higher than the first pressure in a second distillation column having a second reboiler system and a reflux condenser system, to produce a solvent-enriched, second overhead vapor stream and a second bottoms stream, wherein the second bottoms stream is enriched in water compared with the condensed overhead stream;
  (g) performing a first membrane separation step, comprising:
    (i) providing a first membrane having a first feed side and a first permeate side, the membrane being selective in favor of water over solvent;
    (ii) passing at least a portion of the second overhead vapor stream at a first feed pressure across the first feed side;
    (iii) maintaining a first permeate pressure on the first permeate side that is lower than the first feed pressure;
    (iv) withdrawing from the first feed side, as a first residue stream, a dehydrated product stream; and
    (v) withdrawing from the first permeate side a first permeate stream enriched in water compared with the second overhead vapor stream;
  (h) performing a second membrane separation step, comprising:
    (i) providing a second membrane having a second feed side and a second permeate side, the membrane being selective in favor of water over solvent;
    (ii) passing at least a portion of the first residue stream at a second feed pressure across the second feed side;
    (iii) maintaining a second permeate pressure on the second permeate side that is lower than the second feed pressure;
    (iv) withdrawing from the second feed side, as a second residue stream, a dehydrated product stream; and
    (v) withdrawing from the second permeate side a second permeate stream enriched in water compared with the first residue stream.

21. The process of claim 20, wherein the first pressure is within the range of about 0.3 bar to about 1.2 bar.

22. The process of claim 20, wherein the first overhead vapor stream is compressed to a pressure that is great enough to raise the dew point sufficiently that the first overhead vapor stream can be condensed in the first reboiler system.

23. The process of claim 20, wherein the second pressure is within the range of about 2 bar to about 5 bar.

24. The process of claim 20, wherein the solvent comprises ethanol.

25. The process of claim 24, wherein the first membrane has a selectivity in favor of water over ethanol within the range of about 20 to about 200.

26. The process of claim 24, wherein the second membrane has a selectivity in favor of water over ethanol within the range of about 20 to about 200.

27. The process of claim 20, wherein the process further includes the step of recirculating at least a portion of the first permeate stream to the first distillation step.

28. The process of claim 27, wherein the at least a portion of the first permeate stream is compressed before being recirculated to the first distillation step.

29. The process of claim 20, wherein the process further includes the step of recirculating at least a portion of the second permeate stream to the second distillation step.

30. The process of claim 29, wherein the at least a portion of the second permeate stream is compressed before being recirculated to the second distillation step.

31. The process of claim 20, wherein the process further includes the step of recirculating at least a portion of the second residue stream to the first reboiler system as a heating stream.

32. The process of claim 31, wherein at least a portion of the second residue stream is passed through a molecular sieve dryer prior to being recirculated to the first reboiler system.

33. The process of claim 20, wherein the process further includes the step of condensing and withdrawing at least a portion of the second residue stream as a high-purity solvent stream.

34. A process for recovering an organic solvent from a solvent and water mixture, comprising:
  (a) subjecting at least a first portion of the mixture to a first distillation step, carried out by passing a first feed stream of the mixture, at a first pressure, into a first distillation column having a first reboiler system which includes a first heat exchanger, to produce a solvent-enriched, first overhead vapor stream and a first bottoms stream, wherein the first bottoms stream is enriched in water compared with the first feed stream;
  (b) compressing at least a portion of the first overhead vapor stream to form a compressed overhead vapor stream;
  (e) recovering heat by passing at least a portion of the compressed overhead vapor stream through the heat exchanger as a heating stream;
  (d) condensing at least a portion of the compressed overhead vapor stream to form a condensed overhead stream;
  (e) pumping at least a portion of the condensed overhead stream to a second distillation step, carried out under a second pressure that is higher than the first pressure in a second distillation column having a second reboiler system and a reflux condenser system, to produce a solvent-enriched, second overhead vapor stream and a second bottoms stream, wherein the second bottoms stream is enriched in water compared with the condensed overhead stream;

(f) performing a membrane separation step, comprising:
  (i) providing a membrane having a feed side and a permeate side, the membrane being selective in favor of water over solvent;
  (ii) passing at least a portion of the second overhead vapor stream at a feed pressure across the feed side;
  (iii) maintaining a permeate pressure on the permeate side that is lower than the feed pressure;
  (iv) withdrawing from the feed side, as a residue stream, a dehydrated product stream; and
  (v) withdrawing from the permeate side a permeate stream enriched in water compared with the second overhead vapor stream;

(g) condensing and withdrawing at least a portion of the residue stream as a high-purity solvent stream;

whereby energy is provided to the first reboiler system by passing to the first reboiler system at least a portion of one or more of the streams selected from the second overhead vapor stream and the residue stream.

35. The process of claim 34, wherein the first pressure is within the range of about 0.3 bar to about 1.2 bar.

36. The process of claim 34, wherein the first overhead vapor stream is compressed to a pressure that is great enough to raise the dew point sufficiently that the first overhead vapor stream can be condensed in the first reboiler system.

37. The process of claim 34, wherein the second pressure is within the range of about 2 bar to about 5 bar.

38. The process of claim 34, wherein the solvent comprises ethanol.

39. The process of claim 38, wherein the membrane has a selectivity in favor of water over ethanol within the range of about 20 to about 200.

40. The process of claim 34, wherein a condensed liquid product from the heat exchanger is sent as a reflux liquid to the second distillation step.

41. The process of claim 34, wherein at least a portion of the second overhead vapor stream is recirculated to the second distillation step.

42. The process of claim 34, wherein at least a portion of the permeate stream is recirculated to the first distillation step.

43. The process of claim 42, wherein the at least a portion of the permeate stream is compressed before being recirculated to the first distillation step.

44. The process of claim 42, wherein at least a portion of the permeate stream is recirculated to the first distillation step without condensation.

\* \* \* \* \*